United States Patent [19]

Rocco et al.

[11] Patent Number: 5,656,288

[45] Date of Patent: Aug. 12, 1997

[54] STABLE PHARMACEUTICAL COMPOSITIONS CONTAINING TILUDRONATE HYDRATES AND PROCESS FOR PRODUCING THE PHARMACEUTICAL COMPOSITIONS

[75] Inventors: William Rocco, Reading; Sharon M. Laughlin, Phoenixville, both of Pa.

[73] Assignee: Sanofi Winthrop, Inc., New York, N.Y.

[21] Appl. No.: 488,986

[22] Filed: Jun. 8, 1995

[51] Int. Cl.$^6$ ............... A61K 9/16; A61K 9/20; A61K 9/46; A61K 9/48

[52] U.S. Cl. ............ 424/451; 424/464; 424/466; 424/489

[58] Field of Search .................. 424/464, 466, 424/451, 489

[56] References Cited

U.S. PATENT DOCUMENTS

5,405,994  4/1995  Bonnery et al. .............. 562/21

*Primary Examiner*—Thurman K. Page
*Assistant Examiner*—James M. Spear
*Attorney, Agent, or Firm*—William J. Davis; Imre Balogh

[57] ABSTRACT

Disodium tiludronate tetrahydrate is provided for use in pharmaceutical compositions for oral administration in the form of a tablet, effervescent composition, capsule and the like.

11 Claims, 13 Drawing Sheets

STABLE PHARMACEUTICAL COMPOSITIONS CONTAINING TILUDRONATE HYDRATES AND PROCESS FOR PRODUCING THE PHARMACEUTICAL COMPOSITIONS

BACKGROUND OF THE INVENTION

1. Field of the Invention

The present invention relates to pharmaceutical compositions containing tiludronate hydrates for oral administration and a process for their preparation. The pharmaceutical compositions are stable and possess therapeutic properties permitting their use in the treatment of osteoporosis, rheumatoid polyarthritis and Paget's disease.

2. Reported Developments

Bisphosphonic acid derivatives having the formula in which $R_1$ represents a hydrogen atom, a halogen atom, a hydroxyl, an amino or a dialkyl($C_1$–$C_4$)amino, and

$R_2$ represents a halogen atom, a linear alkyl containing from 1 to 5 carbon atoms which is unsubstituted or substituted by a chlorine atom, a hydroxyl, an amino or a dialkyl($C_1$–$C_4$)amino, or $R_2$ represents a phenoxy, a phenyl, a thiol, a phenylthio, a chlorophenylthio, a pyridyl or a thiomorpholin-4-yl, and their salts with pharmaceutically acceptable mineral or organic acids, are known compounds having been disclosed in the following patents:

BE No. 902308
BE No. 865434
FR No. 2531088
JP No. 55-98193
BE No. 822930
DE No. 2130794
EP No. 203649
EP No. 162510
EP No. 39033
EP No. 100718
EP No. 186405
FR No. 2525223
U.S. Pat. No. 4,134,969
U.S. Pat. No. 4,578,376
U.S. Pat. No. 4,621,077
U.S. Pat. No. 4,980,171
U.S. Pat. No. 5,405,994
WO No. 86/00902
WO No. 87/03598

The compounds have been described as useful in the oral treatment of bone diseases and/or articular complaints of the arthritis type. Among the compounds is tiludronic acid, i.e., 4-chlorophenylthiomethylenebisphosphonic acid, and its disodium salt having the chemical structure which has been extensively investigated for the development of a drug useful in the treatment of rheumatoid polyarthritis, Pagers disease and osteoporosis.

U.S. Pat. No. 5,405,994 discloses two forms of disodium tiludronate: disodium tiludronate hemihydrate and disodium tiludronate monohydrate. Disodium tiludronate hemihydrate is prepared in situ from an aqueous solution of tiludronic acid by the addition of a sufficient amount of sodium hydroxide to being the pH to between 4.6 and 4.8. Disodium tiluclronate monohydrate is prepared by heating disodium tiludronate hemihydrate in aqueous solution at a temperature of between 60° C. to 90° C. for about 2 to 24 hours, cooling the solution to a temperature of between room temperature and 5° C., filtering off the precipitate formed and then drying the precipitate.

The preparation of 4-chlorophenylthiomethylenebisphosphonate, disodium 4-chloro-phenylthiomethylenebisphosphonate hemihydrate and disodium 4-chlorophenylthiomethylene-bisphosphonate monohydrate is described as follows.

A) Preparation of 4-chlorophenylthiomethylenebisphosphnic acid

Tetraisopropyl 4-chlorophenylthiomethylenebisphosphonate is prepared by applying the method described in European patent 100 718. This compound is treated with water and hydrochloric acid and heated at 90° C. for several hours. After cooling, extraction is carried out with dichloroethane. The aqueous phase is concentrated under vacuum to remove the hydrochloric acid and the water. Toluene is added and the residual water is driven off by distillation. 4-Chlorophenylthiomethylenebisphosphonic acid precipitates on cooling. This precipitate is collected by filtration, washed with toluene and dried at a temperature less than or equal to 70° C.

B) Preparation of disodium 4-chlorophenylthiomethylenebisphosphonate hemihydrate Sodium hydroxide, either as pellets or as an aqueous solution, is added to an aqueous suspension of the acid obtained above until the pH is about 4.7. Active charcoal is added and the mixture is clarified by filtration. The filtration is mixed with acetone and the expected salt precipitates at room temperature.

The precipitate is collected by filtration, washed with acetone and dried at a temperature less than or equal to 70° C.

C) Preparation of disodium 4-chlorophenylthiomethylenebisphonate monohydrate An aqueous solution of disodium tiludronate hemihydrate is prepared by mixing 100 g of the salt with 1 liter of water and this solution is clarified by filtration. 2.3 liters of acetone are brought to the reflux point and the above aqueous solution is poured in, reflux being maintained for 3 hours.

The medium is left to return to room temperature and is then cooled for 1 hour at 10° C. The precipitate formed is filtered off and then dried overnight at 60° C. in a ventilated oven to give 95 g of the expected product in the form of crystals.

Pharmaceutical tablets prepared using disodium 4-chlorophenylthiomethylbisphosphonate monohydrate stored for 15 months at room temperature were found to be stable.

It has now been surprisingly found that disodium 4-chlorophenylthiomethylenebisphosphonate also exists as a tetrahydrate. It was also found that the tetrahydrate form of disodium 4-chlorophenylthiomethylenebisphosphonate is more stable at high relative humidity than either the monohydrate or hemihydrate forms and is not convened to either the monohydrate or hemihydrate form thereof at ambient temperature and humidity. This surprising discovery lends itself to both process and product advantages heretofore not realized by the prior art. In the process of preparing disodium 4-chlorophenylthiomethylenebisphosphonate (hereinafter sometimes referred to as tiludronate) disodium 4-chlorophenylthiomethylenebisphosphonate is initially obtained as the tetrahydrate form of disodium tiludronate which has not been recognized by either European Patent No. 100,718 or by U.S. Pat. No. 5,405,994. The disodium tiludronate tetrahydrate is then dried to obtain disodium tiludronate hemihydrate. To obtain the final product, i.e., disodium hemihydrate, used in dosage form, the disodium tiludronate hemihydrate is subjected to wet granulation, during which the disodium hemihydrate is converted to its tetrahydrate form, and the granulate is dried to give the disodium hemihydrate.

The present invention recognizes that the tetrahydrate form of disodium tiludronate is stable throughout this process of conversions and affords several advantages including: the drying step required to convert the initially obtained tetrahydrate to hemihydrate can be eliminated; the need to insure complete conversion of the hemihydrate to the tetrahydrate during wet granulation so as to avoid any product variability that might be caused by the presence in the granulate of a mixture of tetrahydrate and unconverted hemihydrate can be avoided; drying the product at about 60° C. to convert the tetrahydrate to the hemihydrate form of tiludronate can be obviated; and the tetrahydrate form can be used in a drug product to ensure physical stability at high relative humidity.

SUMMARY OF THE INVENTION

In accordance with the invention disodium tiludronate tetrahydrate is provided for use in pharmaceutical compositions for oral administration in the form of a tablet, effervescent composition, capsule and the like.

Disodium tiludronate tetrahydrate is provided by the process of:

(a) reacting tiludronic acid with sodium hydroxide in an aqueous solution and then adding a non-solvent such as acetone to cause precipitation of the tetrahydrate; or (b) subjecting disodium tiludronate hemihydrate to an excess of water; or (c) subjecting disodium tiludronate monohydrate to an excess of water.

DETAILED DESCRIPTION OF THE INVENTION

The effects of humidity on the drug substance disodium tiludronate were investigated by Thermal Gravimetric Analysis (TGA), Fourier Transform Infrared Spectroscopy (FTIR), and X-Ray Powder Diffraction (XRPD). The structure of disodium tiludronate hemihydrate changed to a tetrahydrate form at high humidity (95% RH) and to a mixture of forms at 75–85% RH. The mixture is composed of tetrahydrate and monohydrate or possibly all three forms. The tetrahydrate form was observed to contain 16.4% water, in excellent agreement with the theoretical value (16.6%) for a tetrahydrate. FTIR spectra and XRPD data were significantly different for the tetrahydrate with respect to the unstressed drug substance, thus confirming a crystalline change. At lower relative humidities (12–58% RH), disodium tiludronate hemihydrate showed no changes by TGA and FTIR.

The following describes the studies and results obtained thereby.

Study/Design Methods

A) Hygroscopicity

Samples of disodium tiludronate hemihydrate were stressed at humidity levels of 12–95% RH using different saturated salt solutions to obtain a range of relative humidity. The salt solutions used and the corresponding relative humidity are tabulated below:

| Salt Solution | % RH (20° C.) |
| --- | --- |
| Lithium Chloride | 12 |
| Potassium Acetate | 23 |
| Calcium Chloride | 31 |
| Potassium Carbonate | 43 |
| Sodium Bromide | 58 |
| Sodium Chloride | 75 |
| Potassium Bromide | 84 |
| Sodium Phosphate | 95 |

The samples were held for 2 weeks at each humidity at 20° C. and analyzed by TGA for moisture content. The samples were also analyzed by FTIR to determine if spectroscopic changes were observed. Samples which increased in moisture content after 2 weeks were then moved to lower relative humidity to determine if the water uptake was reversible.

A sample of the monohydrate form was also stressed with respect to humidity. Samples were stressed at 58–95% RH at 20° C. for 2 weeks.

B) Thermal Gravimetric Analysis (TGA)

Thermal Gravimetric Analysis was performed on the Perkin Elmer TGA-7 system. Samples were weighed into a platinum pan and scanned at a rate of 5° C./min. under nitrogen purge gas.

C) Fourier Transform Infrared Spectroscopy (FTIR)

FTIR spectra were obtained on the Nicolet 730 system equipped with an MCT detector. Samples were run as KBr dispersions at approximately 1% concentration.

D) X-Ray Powder Diffraction (XRPD)

XRPD data was provided by Kodak Analytical Technology Division (Rochester, N.Y.) using a Rigaku RU 300 system at 2° C. (2-theta)/min.

E) Solubility

The solubility of unstressed hemihydrate, the monohydrate form and a sample which was equilibrated at 95% RH, i.e. tetrahydrate were compared in acetate buffer. A pH value of 4.8 was chosen. Approximately 250 mg of drug was added to 1 ml of solvent and agitated with a laboratory rotator at 20° C. The sample was filtered (0.45 micron) and diluted (200 ul to 25 ml). This solution was then diluted by a factor of 5 prior to UV analysis. Samples were analyzed at time points of 0.5, 3.0, and 24 hours with the Hewlett Packard 8451A diode array spectrophotometer. Absorbance was measured at 264 nm versus a standard prepared in acetate buffer. The solubility was determined (based on anhydrous drug) for two different samples (of each form) at each time point.

F) Intrinsic Dissolution Rate

The intrinsic dissolution rates of hemihydrate, the monohydrate form and tetrahydrate form were determined in acetate buffer (pH=4.8) at 20° C. A disk (0.5 cm$^2$) was compressed under the following conditions: 225–250 mg drug, 4000 lbs pressure, and 30 seconds compaction time. The disk was dissolved in a Vander Kamp VK 6000 dissolution bath in 250 ml solvent at 100 RPM. Samples were withdrawn at 2, 4, 6, 8, 10 and 15 minutes and diluted by a factor of 2 for UV analysis. Samples were analyzed at 264 nm with the Hewlett Packard 8451A diode array spectrophotometer. Intrinsic dissolution plots were generated by plotting concentration/area vs. time and determining the slope by linear regression. Each dissolution experiment was run in triplicate.

G) Stressing of 200 mg Tablets

Samples of the dosage form were also stressed with respect to humidity. Samples of tablets (200 mg) were stressed at 12–95% RH for 2 weeks.

Results of Study

A) Hygroscopicity

Figure 1A:
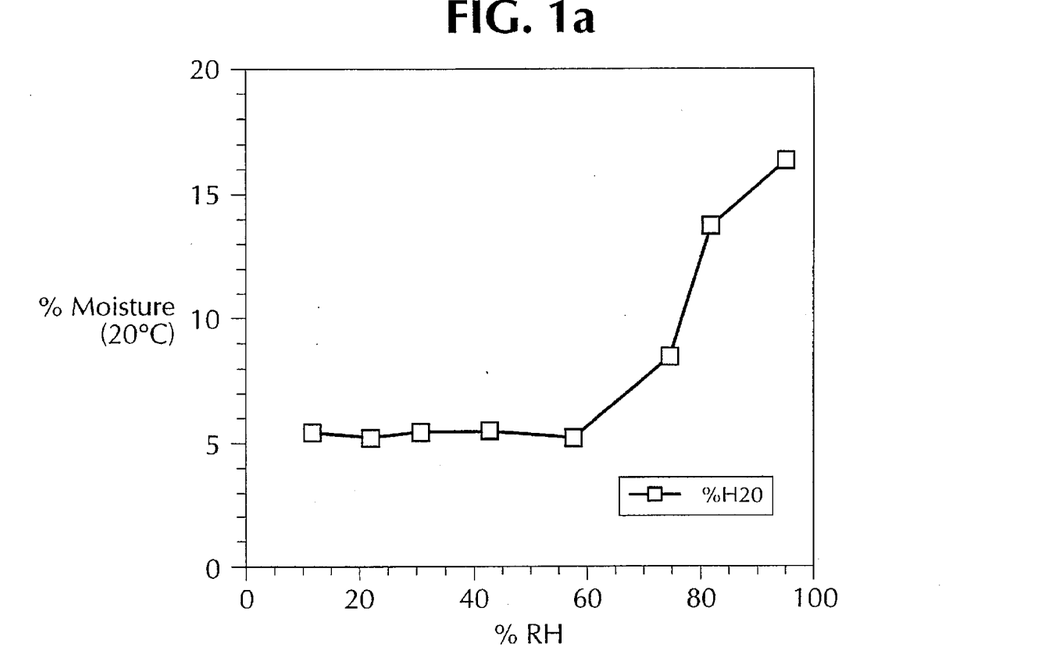
FIGS. 1a, 1b, 2a, 2b, 3, 4a, 4b, 4c, 4d and 5 through 9 display physical characteristics of disodium tiludronate in hemihydrate, monohydrate and tetrahydrate form which will assist in describing the present invention.

The hygroscopicity data is shown in FIG. 1a for hemihydrate samples stressed at a range of relative humidity values. At humidity levels of 12–58% the water content (TGA analysis) remains at approximately 5%, similar to unstressed drug substance. This moisture level is approximately equal to the theoretical moisture content for a monohydrate form (4.7%). However, at higher humidity levels (75–95% RH) significant water uptake is observed. At 95% RH a moisture level of 16.4% was determined. This value closely corresponds to the theoretical value for a tetrahydrate form of tiludronate (16.6%). The sample stressed at 95% RH showed a significant change in the FTIR spectra and X-ray pattern indicative of crystalline rearrangement. The TGA, FTIR, and X-ray powder diffration data confirms the isolation of the tetrahydrate form.

Figure 1B:
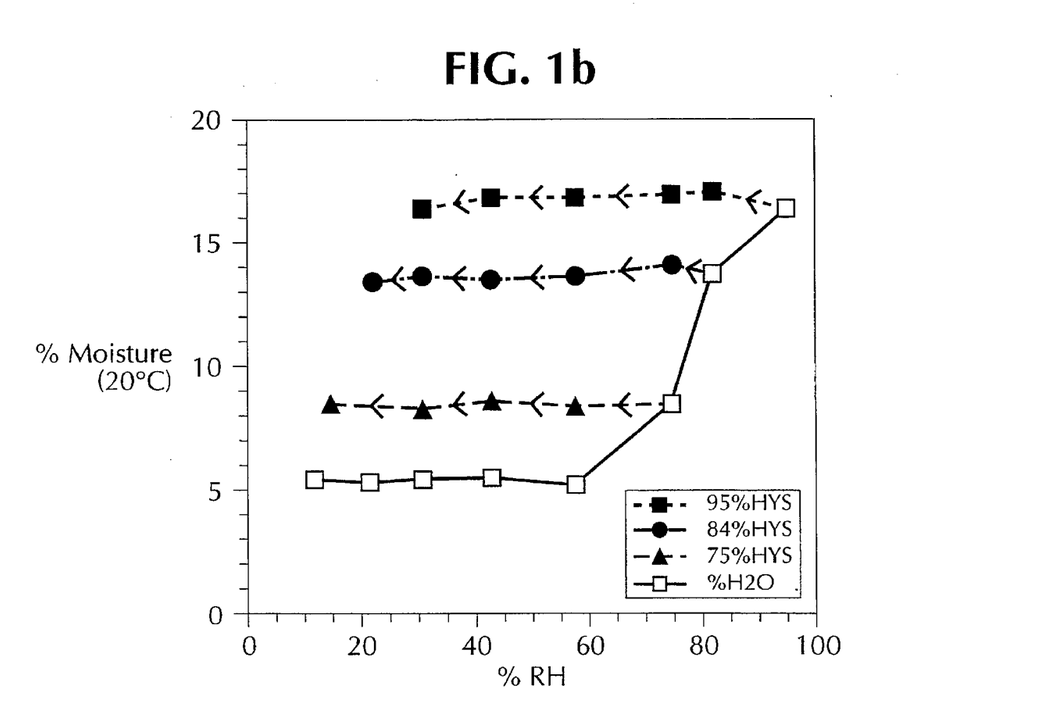

Hysteresis data (samples stored at high humidity were moved from high to low humidity) for samples stressed at 75–95% RH is shown in FIG. 1b. When the samples stressed at 75–95% RH were moved stepwise to lower relative humidity chambers, the moisture level did not decrease. This behavior is indicative of crystalline changes and shows that the moisture uptake is not hygroscopic behavior. If the moisture was hygroscopic in nature one would expect the moisture level to decrease as the humidity level is decreased. The hysteresis data indicated the stability of the tetrahydrate form at humidity levels as low as 31% RH.

Typically a substance which is hygroscopic will increase in moisture content as relative humidity is increased. Tiludronate does not increase in moisture content as relative humidity is increased until a relative humidity is reached where crystalline changes occur.

Figure 2A:
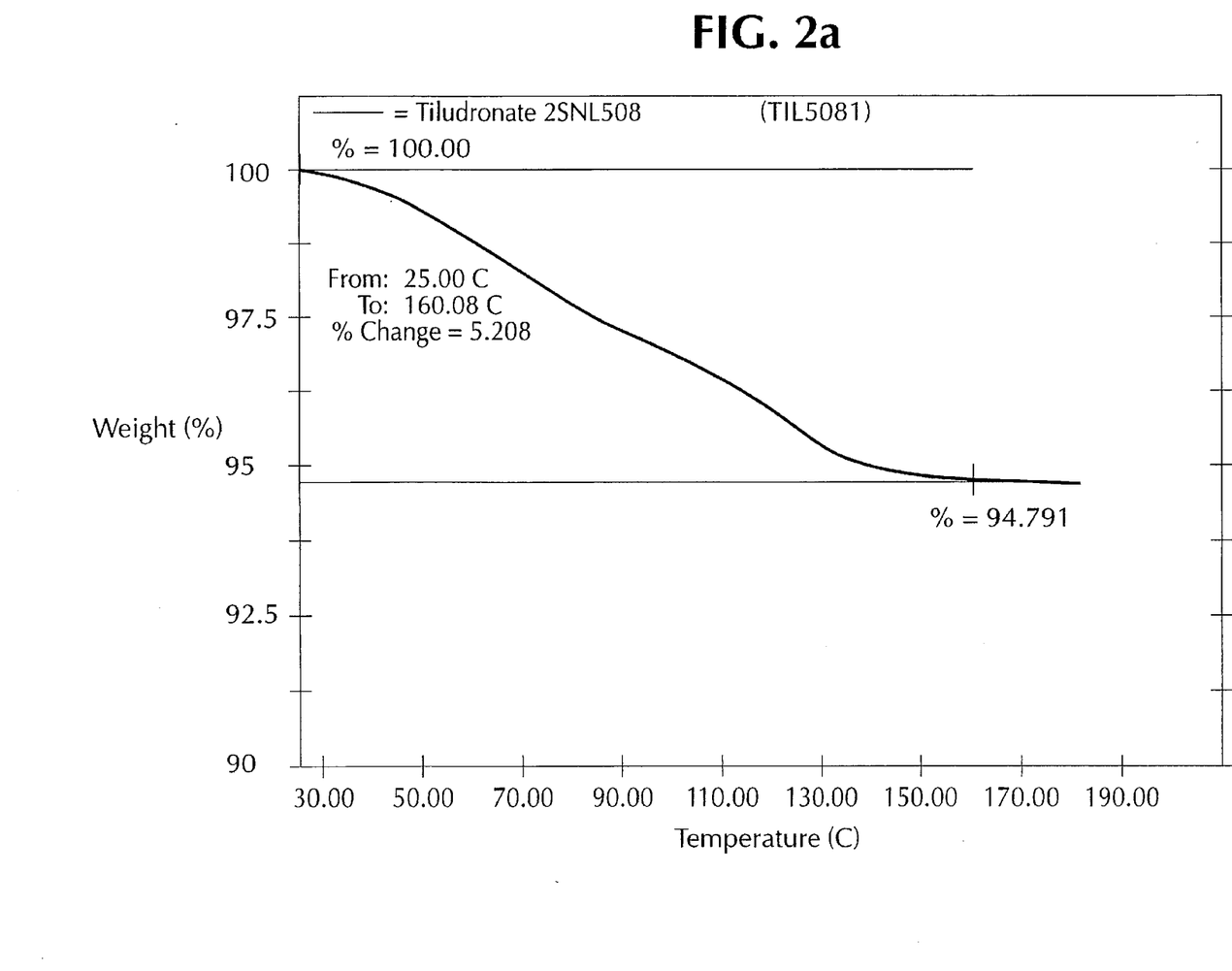
Figure 2B:
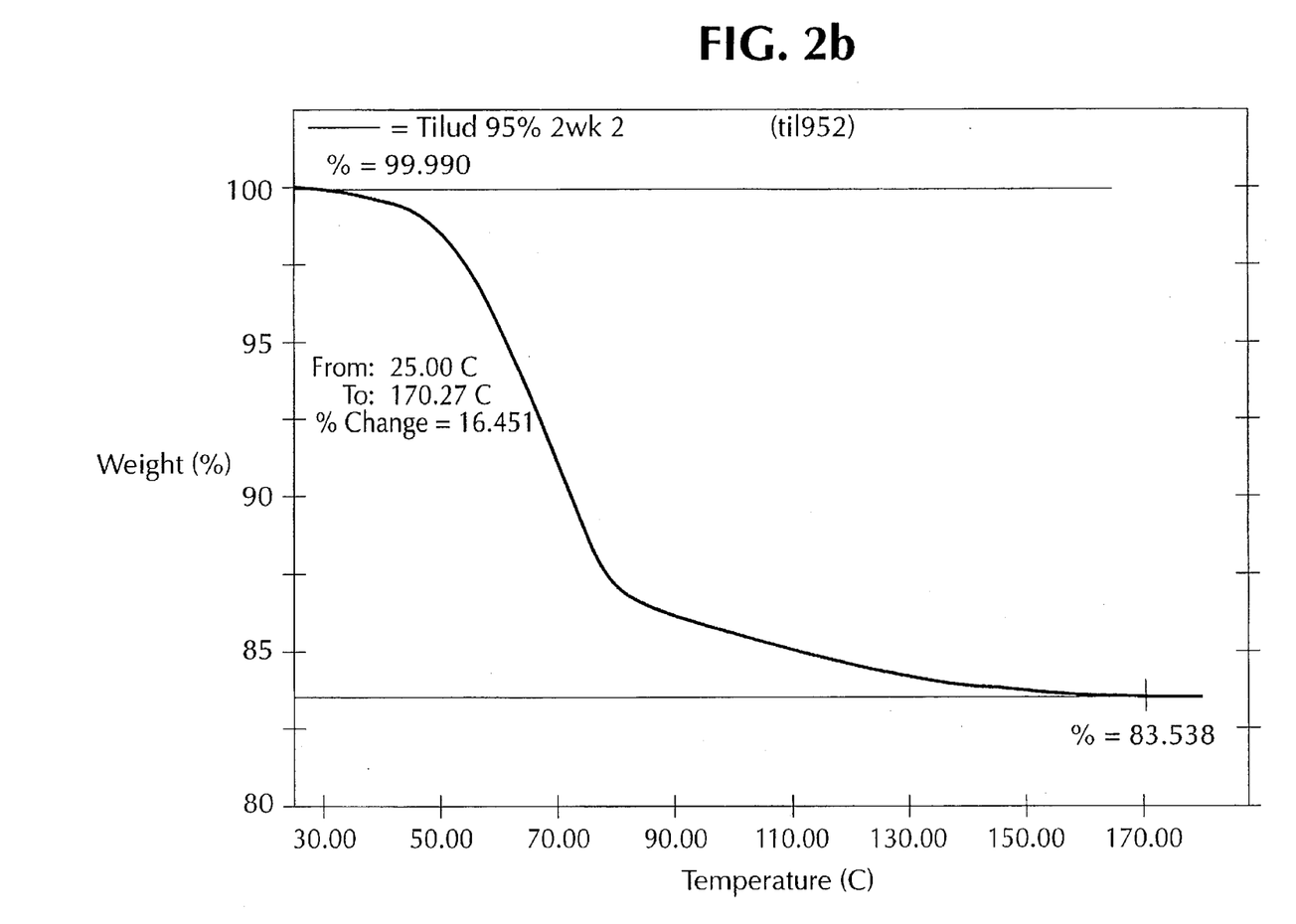
Figure 3:
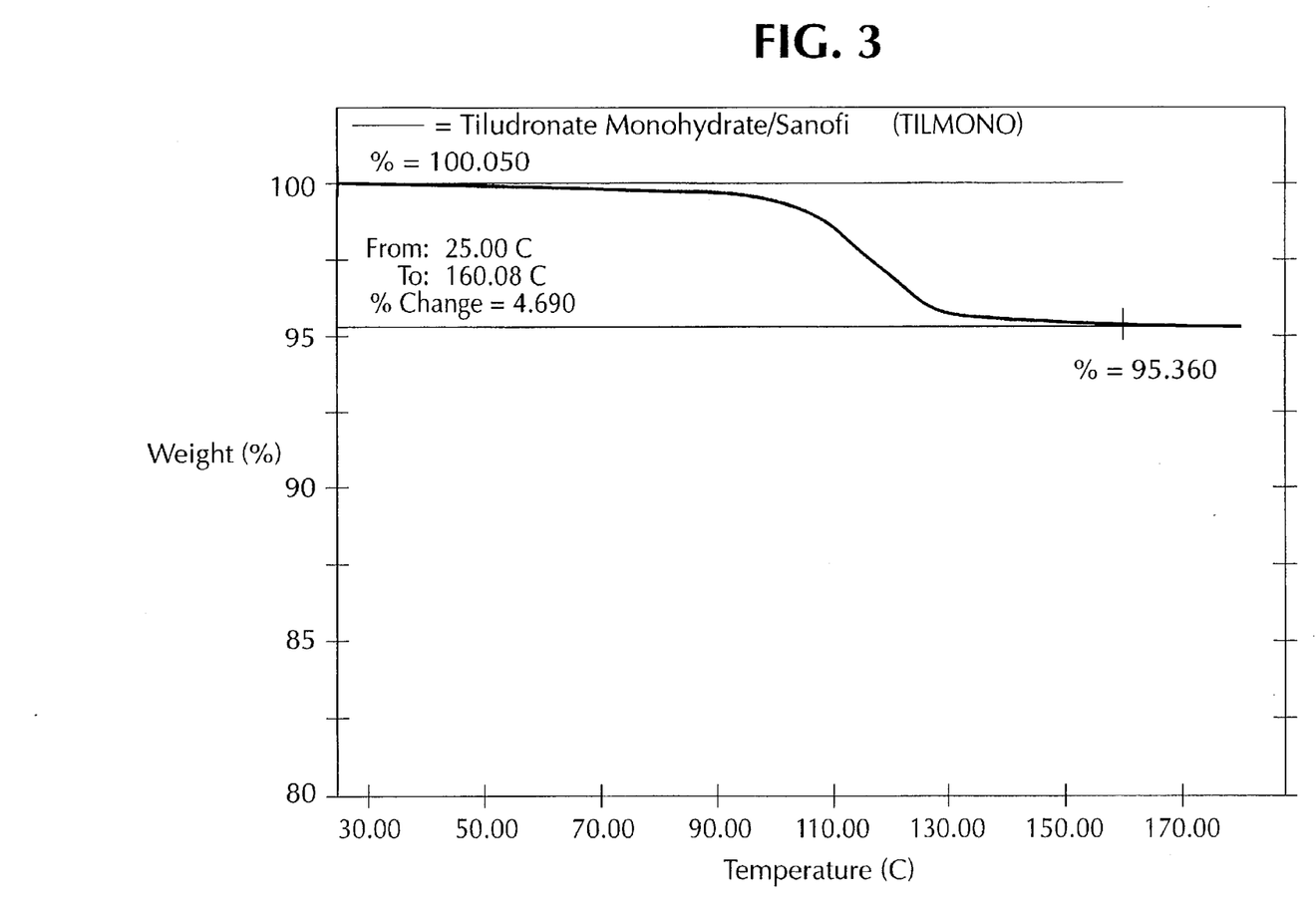

The TGA scan for the hemihydrate is shown in FIG. 2a. The TGA scan for the drug substance which was stressed at 95% RH is shown in FIG. 2b. The total weight loss (16.4%) is similar to the theoretical value for a tetrahydrate of tiludronate (16.6%). If the water was hygroscopic water, then the changes is the XRPD pattern alluded to in section D would not have been significant. FIG. 3 shows TGA data for the monohydrate form run at 5° C. min.

B) FTIR

The FTIR spectra of the hemihydrate samples held at high humidity show evidence of crystalline changes. Samples exhibited no changes in spectra after two weeks storage at relative humidities of 58% and below; these spectra matched the spectra of the starting material.

Figure 4A:
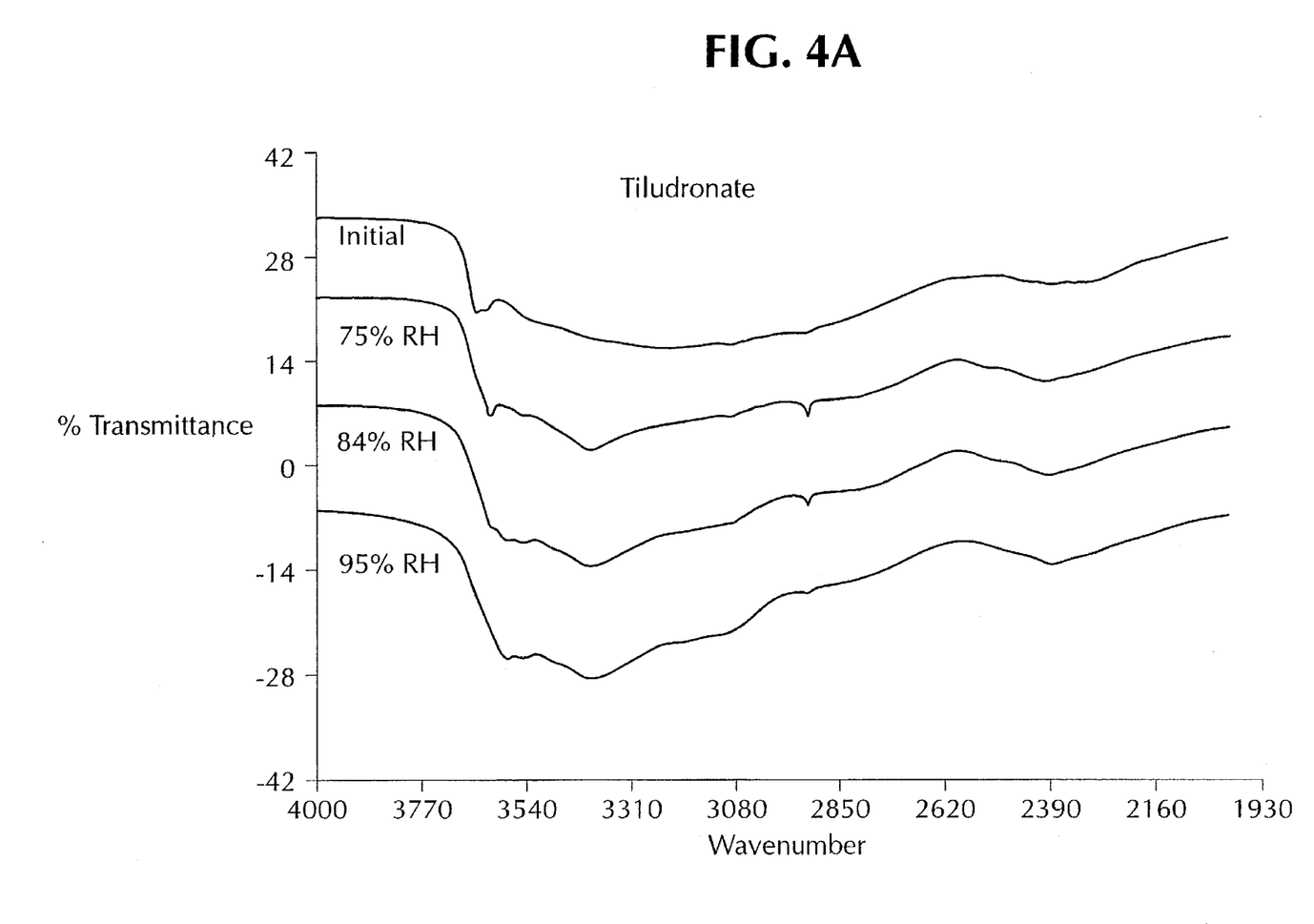
Figure 4B:
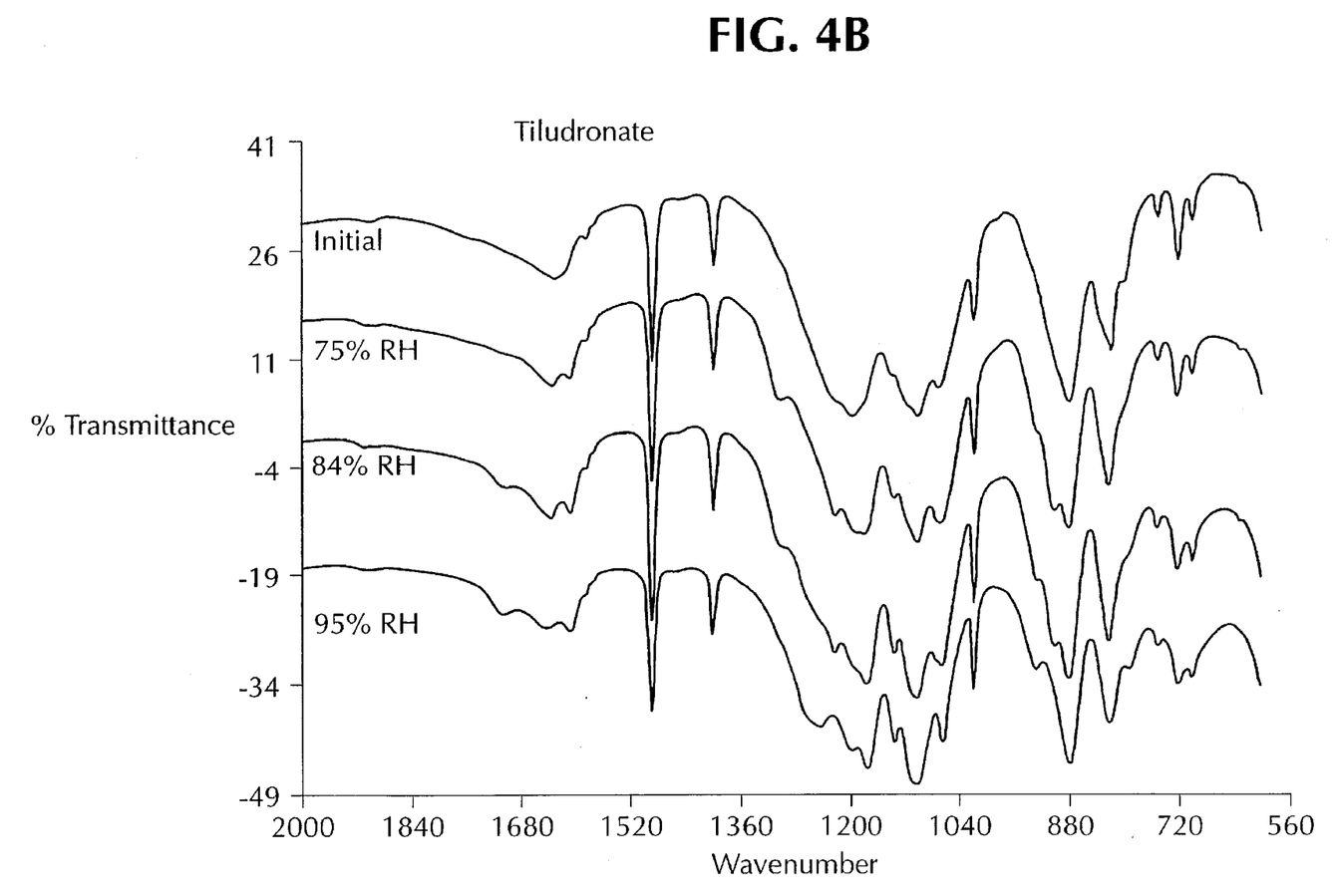

The spectra of the hemihydrate samples stored at 75% RH and 84% RH indicated a partial change to monohydrate and tetrahydrate (FIG. 4a–b). A peak at 2919 cm-1 observed in the 75% RH stressed samples is indicative of the presence of the monohydrate crystal form. The 84% RH sample also appears to contain some fraction of the monohydrate form, mixed with an increasing fraction of the tetrahydrate. Since the water content of these samples were 8.4% and 13.7% at 75% and 84% RH respectively, it appears that the samples may be a mixture of the tetrahydrate and the monohydrate form or possibly all three forms.

At 95% RH the tetrahydrate FTIR spectra shows little evidence of the monohydrate form. The peak locations of the unstressed hemihydrate, 75% RH stressed, and 95% RH stressed are tabulated below. For reference, peak locations for the monohydrate form are included.

| Sample | Peak Location (cm-1) |
|---|---|
| hemihydrate | 3623 3638 1621 |
| 75% RH | 3613 3396 2919 1626 1599 |
| 95% RH-tetrahydrate | 3578 3543 3394 1696 1635 1597 |
| Monohydrate | 3613 3399 2919 1597 |

Figure 4C:
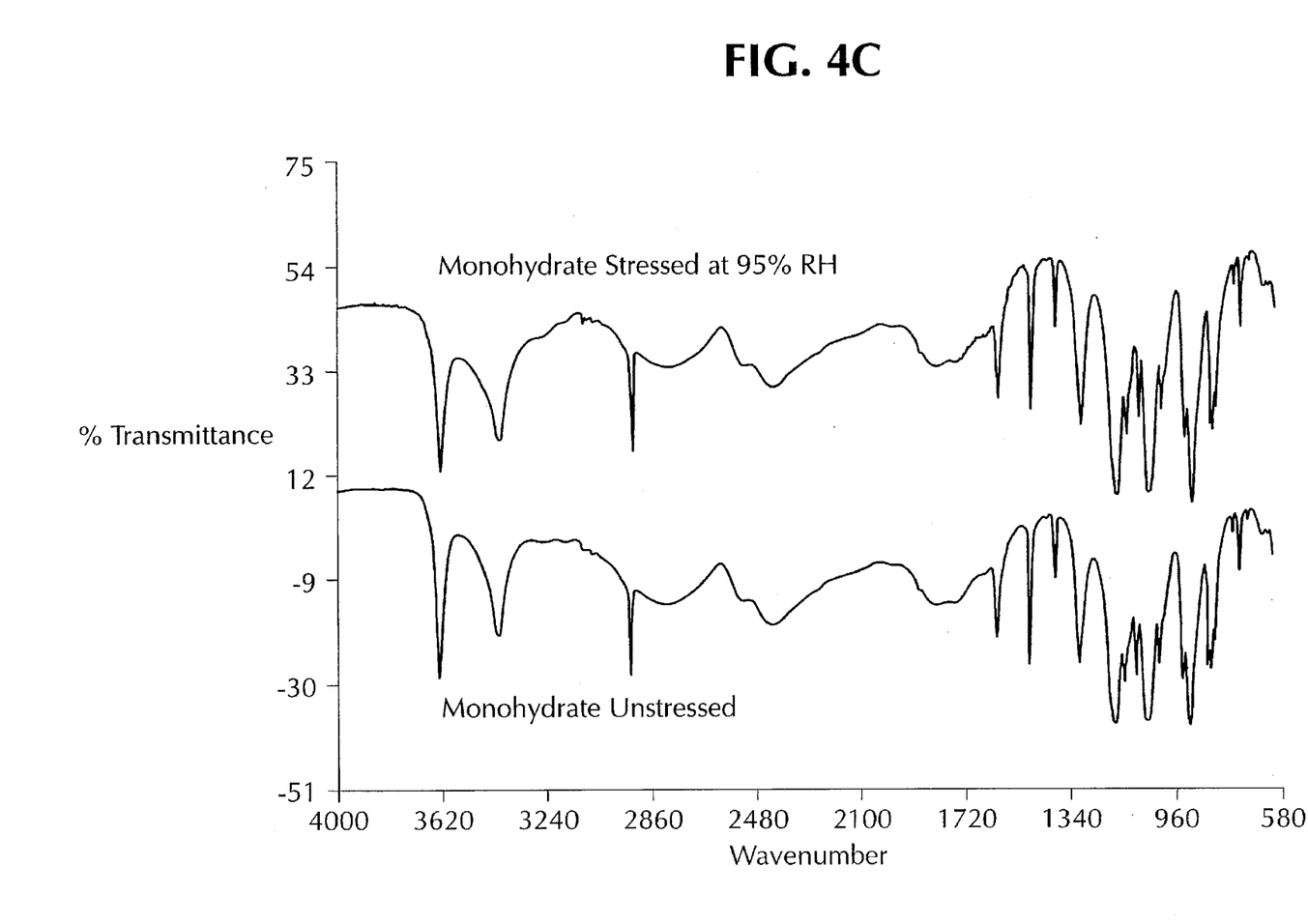
Figure 4D:
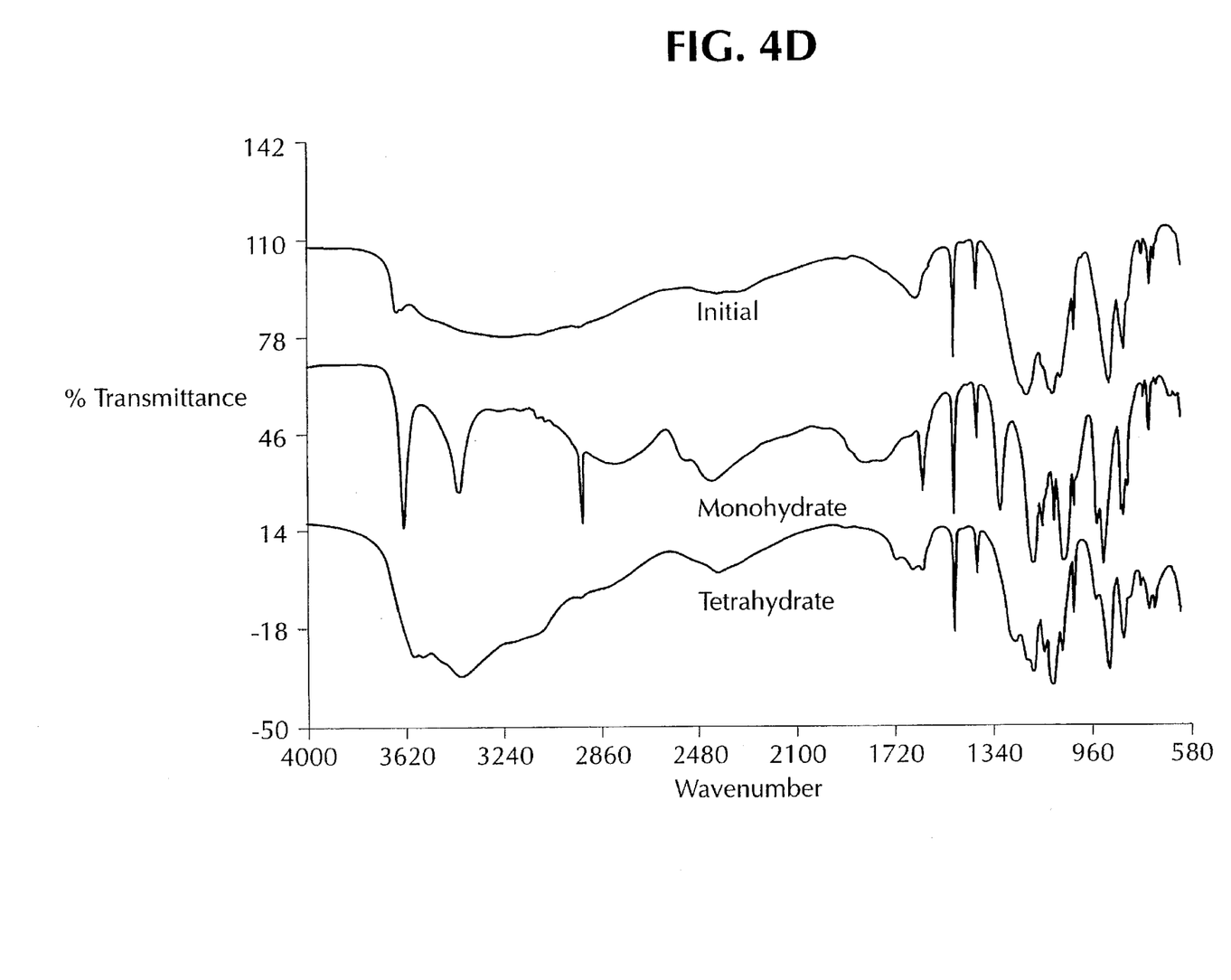

The FTIR spectra of the initial hemihydrate, the monohydrate and the tetrahydrate forms are shown in FIG. 4c. The spectra are unique and indicative of different crystal structures.

D) XRPD

Figure 5:
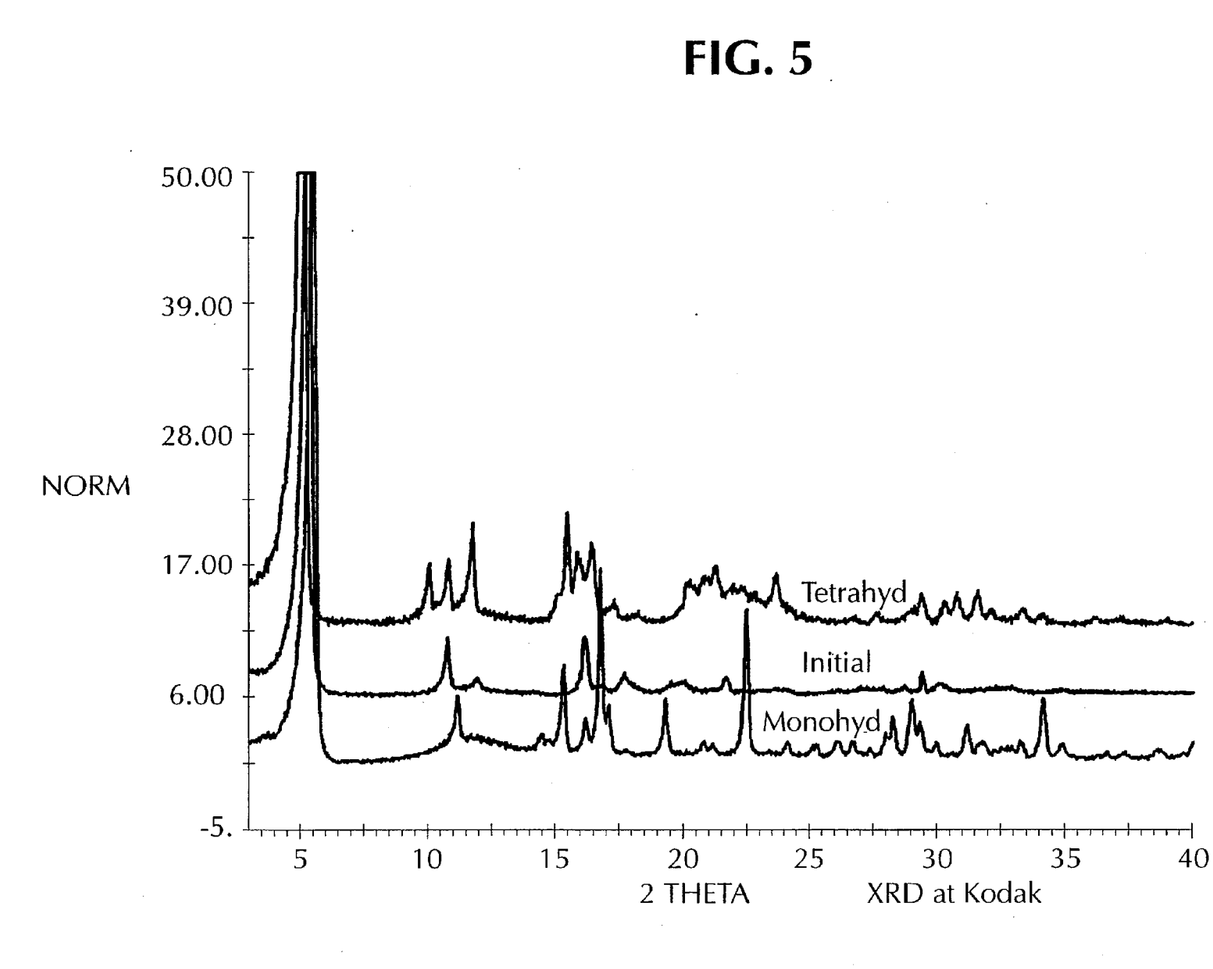

X-Ray powder diffraction patterns for the hemihydrate drug substance and monohydrate forms are compared with a sample of hemihydrate which was stressed at 95% RH in FIG. 5. The patterns for the initial hemihydrate and the stressed drug substance (tetrahydrate) are clearly unique and indicate a rearrangement in internal structure of the drug substance at high humidity rather than hygroscopic behavior. The x-ray data confirmed the conversion of the hemihydrate to the tetrahydrate form.

E) Solubility

Figure 6:
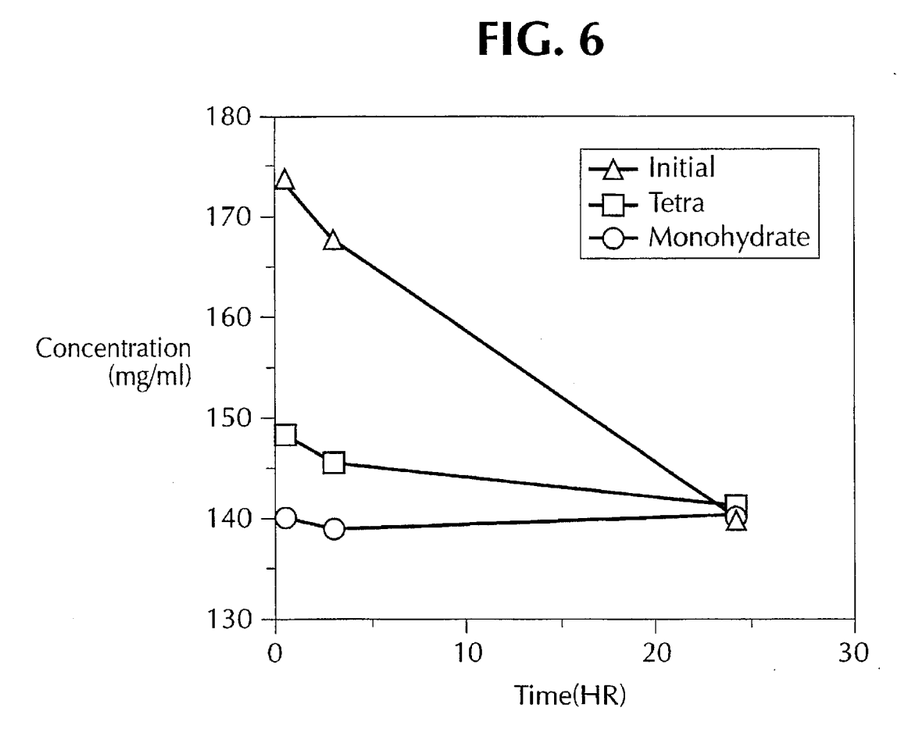

The concentration of tiludronate in acetate buffer solution (pH=4.8) versus time is shown in FIG. 6. The initial solubility of the hemihydrate drug substance and monohydrate form was higher than the tetrahydrate form (hemihydrate stressed at 95% RH). At 0.5 hours a concentration of 147 mg/ml was observed for the unstressed sample while a concentration of 175 mg/ml was observed for the monohydrate form. In contrast, a concentration of 140 mg/ml was observed for the tetrahydrate at 0.5 hours. The concentration of the unstressed hemihydrate sample and the monohydrate decreased with time and at 24 hours was equivalent to the tetrahydrate. FTIR analysis of the residual solid in the hemihydrate and monohydrate samples indicated conversion to the tetrahydrate. This explains the decrease in solubility with time.

F) Intrinsic Dissolution Rate

Figure 7:
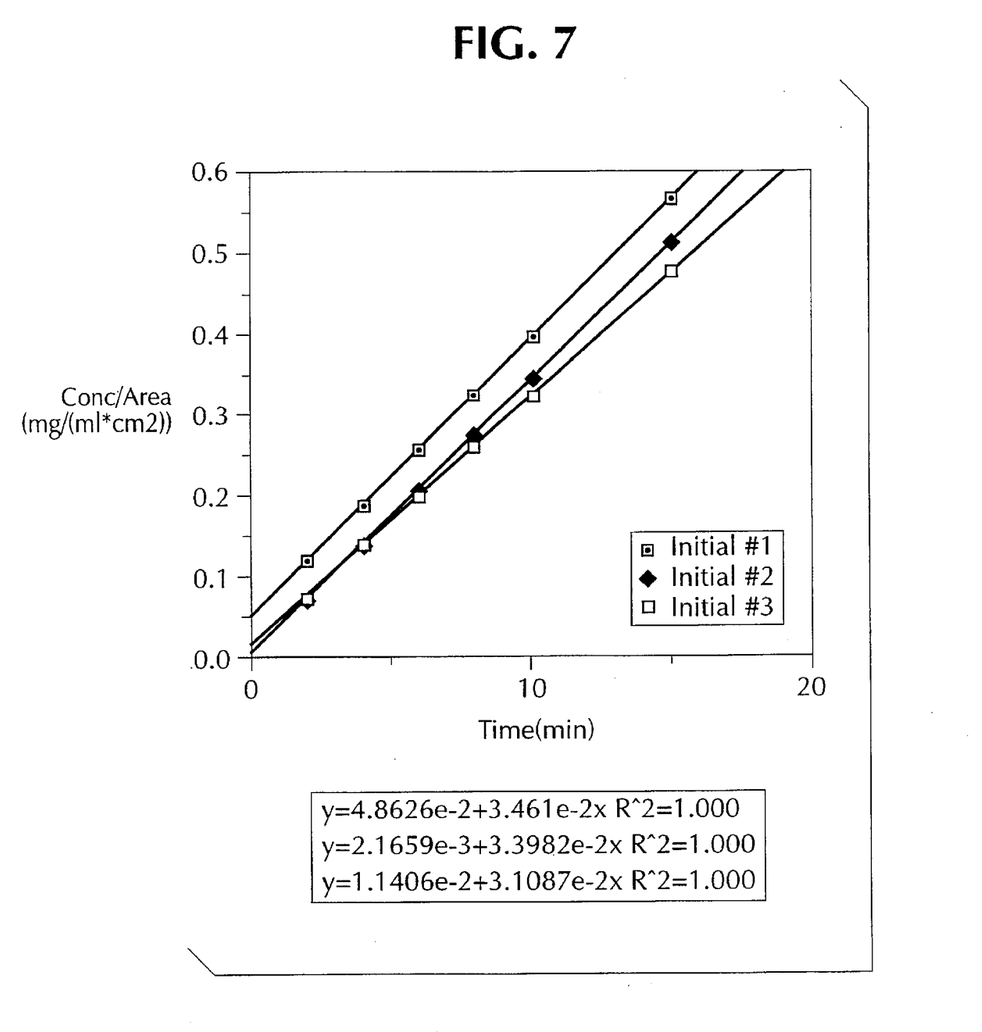
Figure 8:
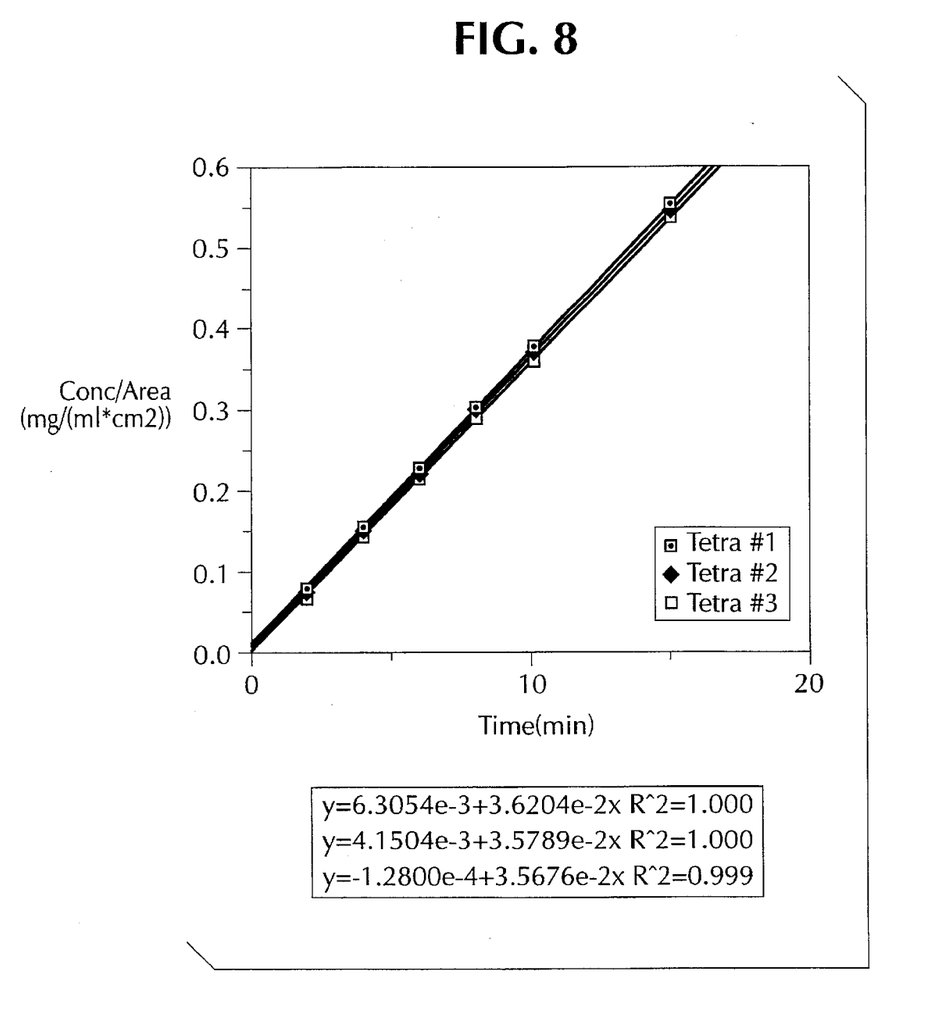
Figure 9:
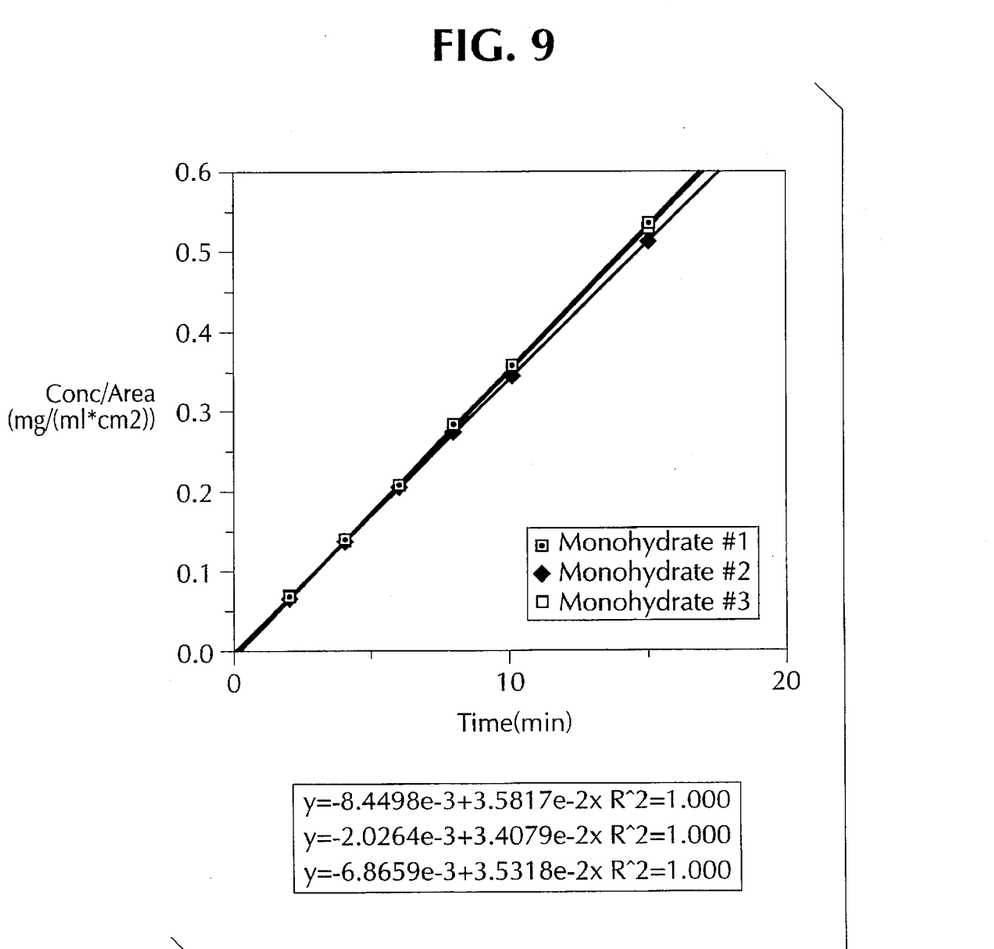

Intrinsic dissolution rate experiments were run on the hemihydrate drug substance, the monohydrate form, and the tetrahydrate form (hemihydrate stressed at 95% RH). FIGS. 7–9 show data for each form in triplicate. The average slopes were similar for the tetrahydrate form (0.0359 mg/(ml*cm$^2$*min) versus the monohydrate form of the drug substance (0.0351 mg/(ml*cm$^2$*min), while the hemihydrate drug substance was slightly lower (0.0332 mg/(ml*cm$^2$*min). FTIR analysis of the disk for the hemihydrate drug substance at the end of the experiment indicated conversion to the tetrahydrate form was occurring, thus making data interpretation difficult. The monohydrate disk did not show transformation to the tetrahydrate at the end of the experiment but it is possible the thickness of the transformation layer is small and therefore difficult to remove and analyze.

G) Stressing of Tablets

The FTIR spectrum of the unstressed tablet was similar to the spectrum of the unstressed drug substance due to the high drug content of the tablet. The FTIR spectra of the samples held at high humidities show evidence of crystalline changes. The spectrum of the sample stressed at 95% RH for one week indicated transformation to the monohydrate and tetrahydrate forms. The presence of peaks at 3613 cm-1 and 2920 appear to be related to the presence of the monohydrate form, mixed with a fraction of the tetrahydrate. The tablet stored at 95% RH appeared to contain predominantly the tetrahydrate form, although the FTIR spectrum showed some fraction of the monohydrate form.

In summary, the changes which occurred in the FTIR spectra and X-ray powder diffraction pattern of disodium tiludronate hemihydrate which was stressed at 95% RH clearly indicate that crystalline changes accompany the increase in moisture content. This indicates that the increased moisture was not hygroscopic moisture. The level of moisture observed after two weeks at 95% RH (16.4%) closely corresponds to the theoretical value for a tetrahydrate form of disodium tiludronate (16.6%). The TGA, FTIR, and X-ray data confirm the existence of a tetrahydrate form. Increased moisture content at 75% and 85% appear to indicate partial transformation to the tetrahydrate form. The FTIR spectra of these samples (stressed at 75% and 84% RH) indicated the presence of the monohydrate form. The increased moisture at 75–95% RH was not reversible; these samples retained the moisture when moved to lower relative humidity. The moisture uptake at 95% RH was retained and the sample did not revert at 31% RH.

Disodium tiludronate tetrahydrate is incorporated into a pharmaceutical composition which comprises of from about 1 to about 99% w/w of disodium tiludronate tetrahydrate and of from about 99 to about 1% w/w of a pharmaceutically acceptable carrier. The pharmaceutical composition can be in the form of tablets, capsules, powders, granules, drops and the like which can be administered orally. The tablet form is preferred. The pharmaceutical composition can contain ingredients customarily used in pharmacy for the preparation of oral forms.

Thus, the composition according to the invention may contain a disintegrating agent, a flowing agent, a lubricant and any suitable bulking excipient. The composition may also contain adjuvants, e.g. absorption enhancers such as sodium lauryl sulfate.

Lactose, cellulose or starches can be used as the bulking excipient. Stearic acid, magnesium stearate, L-leucine or, for example, glycerol tribehenate can be used as the lubricant. Sodium carboxymethyl starch and crosslinked polyvinylpyrrolidone can be used as the disintegrating agent. Pure silica or colloidal silicon dioxide can be used as the flowing agent.

The present invention further relates to instantaneously dissolving oral forms and to effervescent oral forms obtained by adding an effervescent pair of compounds to the composition according to the invention. Examples of effervescent pairs of compounds which can be used are tartaric acid and sodium bicarbonate or citric acid and sodium bicarbonate.

The tablet form is a preferred form according to the invention. The invention further relates to instantaneously dissolving tablets, effervescent tablets and coated tablets.

The pharmaceutical compositions are described as Examples and in no way limit the scope of the invention.

EXAMPLE 1

Wet Granulation

Tiludronate tetrahydrate, sodium lauryl sulfate, polyvinylpyrrolidone and lactose were combined as dry ingredients and passed through a 30 mesh screen to obtain a uniform blend.

Hydroxy propyl methyl cellulose was dissolved in purified water which was preheated to about 65° C.

To the blend of dry ingredients the hydroxy propyl methyl cellulose was slowly added while mixing to obtain a wet granulate which was then passed through a 10 mesh screen. The wet screened granulate was dried at a temperature of about 25°–35° C. to remove excess water. The so-obtained granulate was tableted with standard equipment and procedure according to accepted pharmaceutical practices.

| Tablets | |
| --- | --- |
| Tiludronate tetrahydrate | 267 mg |
| Sodium lauryl sulfate (SLS) | 4.5 mg |
| Hydroxyl propyl methyl cellulose | 5.25 mg |
| Polyvinylpyrrolidone (PVPP) | 15.0 mg |
| Lactose | 4.5 mg |
| for a finished tablet of | 300 mg |
| Water* (approximately 1 mg/2.5 mg drug) | |

*Removed during processing

EXAMPLE 2

Example of Tetrahydrate Preparation 60 g of tiludronate disodium hemihydrate is dissolved in 600 mL water at 20° C.–25° C. Approximately 600 mL acetone is slowly added to cause a precipitate. The precipitate is agitated at 200° C.–25° C. for several hours and then filtered and air dried at 25° C.–30° C. moisture content of the product is approximately 16.69 by TGA.

EXAMPLE 3

| Tablets | |
| --- | --- |
| Disodium tiludronate tetrahydrate | 267 mg |
| Sodium laurylsulfate | 4.5 mg |
| Crosslinked sodium carboxymethyl cellulose | 24 mg |
| Microcrystalline cellulose | 150 mg |
| Magnesium stearate | 4.5 mg |
| | 450 mg |

EXAMPLE 4

| Tablets | |
|---|---|
| Disodium tiludronate tetrahydrate | 267 mg |
| Sodium laurylsulfate | 8 mg |
| Crosslinked sodium carboxymethyl cellulose | 24 mg |
| Lactose | 146.5 mg |
| Magnesium stearate | 4.5 mg |
| | 450 mg |

EXAMPLE 5

A tablet having the following composition is prepared by dry granulation:

| | |
|---|---|
| Disodium tiludronate tetrahydrate | 267 mg |
| Sodium laurylsulfate | 4.5 mg |
| Anhydrous colloidal silica | 1.3 mg |
| Microcrystalline cellulose | 21.6 mg |
| Crosslinked polyvinylpyrrolidone | 8.0 mg |
| Magnesium stearate | 5.6 mg |
| Anhydrous lactose for a finished tablet of: | 320 mg |

EXAMPLE 6

A tablet having the following composition is prepared by wet granulation:

| | |
|---|---|
| Disodium tiludronate tetraydrate | 267 mg |
| Sodium laurylsulfate | 4.5 mg |
| Methyl hydroxypropyl cellulose | 5.25 mg |
| Crosslinked polyvinylpyrrolidone | 15.0 mg |
| Magnesium stearate | 0.60 mg |
| Purified water | |
| Lactose for a finished tablet of | 300 mg |

Having described the invention with reference to its preferred embodiments, it is to be understood that modifications within the scope of the invention will be apparent to those skilled in the art.

What is claimed is:

1. A process of making a pharmaceutical composition comprising the steps of: subjecting disodium tiludronate monohydrate to an excess water to obtain disodium tiludronate tetrahydrate; and compounding the disodium tiludronate tetrahydrate with a pharmaceutically acceptable carrier.

2. A pharmaceutical composition comprising an effective amount of disodium tiludronate tetrahydrate and a pharmaceutically acceptable carrier comprising sodium lauryl sulfate.

3. The pharmaceutical composition of claim 2 in a form suitable for oral administration.

4. The pharmaceutical composition of claim 2 in tablet form.

5. The pharmaceutical composition of claim 2 in effervescent oral form.

6. A pharmaceutical composition comprising an effective amount of disodium tiludronate tetrahydrate and a pharmaceutically acceptable carrier comprising sodium lauryl sulfate in capsule form.

7. A process of preparing disodium tiludronate tetrahydrate comprising: reacting tiludronic acid with sodium hydroxide in an aqueous solution.

8. A process of preparing disodium tiludronate tetrahydrate comprising: subjecting disodium tiludronate hemihydrate to an excess of water.

9. A process of preparing disodium tiludronate tetrahydrate comprising: subjecting disodium monohydrate to an excess of water.

10. A process of making a pharmaceutical composition comprising the steps of: preparing disodium tiludronate tetrahydrate by reacting tiludronic acid with sodium hydroxide in an aqueous solution; and compounding the so-obtained disodium tiludronate tetrahydrate with a pharmaceutically acceptable carrier.

11. A process of making a pharmaceutical composition comprising the steps of: subjecting disodium tiludronate hemihydrate to an excess water to obtain disodium tiludronate tetrahydrate; and compounding the disodium tiludronate tetrahydrate with a pharmaceutically acceptable carrier.

* * * * *